United States Patent [19]

Roosdorp et al.

[11] Patent Number: 5,618,786

[45] Date of Patent: Apr. 8, 1997

[54] AEROSOLIZATION OF PROTEIN THERAPEUTIC AGENT

[75] Inventors: Nicolaas J. Roosdorp, Foster City, Calif.; Ronald G. Crystal, Washington, D.C.

[73] Assignees: Cooper Laboratories, Inc., Mountain View, Calif.; The United States of America as represented by the Department of Health and Human Services, Washington, D.C.

[21] Appl. No.: 208,491

[22] Filed: Mar. 9, 1994

Related U.S. Application Data

[63] Continuation of Ser. No. 873,640, Apr. 23, 1992, abandoned, which is a continuation of Ser. No. 504,047, Apr. 3, 1990, abandoned, which is a continuation of Ser. No. 44,446, Apr. 30, 1987, abandoned.

[51] Int. Cl.$^6$ ..................................................... A61K 38/43
[52] U.S. Cl. .............................. 514/8; 514/2; 424/199.1; 530/324; 435/218
[58] Field of Search ........................... 514/8, 2; 424/89, 424/199.1; 530/324; 435/218

[56] References Cited

U.S. PATENT DOCUMENTS

| | | |
|---|---|---|
| 3,642,981 | 2/1972 | Cuculis et al. |
| 4,485,100 | 11/1984 | Hochstrasser et al. ............... 424/177 |
| 4,595,674 | 6/1986 | Tschesche et al. ..................... 514/9 |
| 4,711,848 | 12/1987 | Insley et al. .......................... 435/91 |
| 4,732,973 | 3/1988 | Barr et al. ............................ 530/350 |
| 4,895,719 | 1/1990 | Radhakrishnan et al. ............. 424/45 |
| 4,916,117 | 4/1990 | Lezdey et al. ........................ 514/8 |
| 4,997,814 | 3/1991 | Hammond ............................ 514/8 |
| 5,093,316 | 3/1992 | Lezdey et al. ........................ 514/12 |
| 5,215,965 | 6/1993 | Lezdey et al. ........................ 514/8 |

FOREIGN PATENT DOCUMENTS

| | | |
|---|---|---|
| 0103409 | 3/1984 | European Pat. Off. . |
| 0073251 | 6/1986 | European Pat. Off. . |
| 0189784 | 11/1989 | European Pat. Off. . |
| 2205307 | 5/1974 | France . |
| 56-128721 | 10/1981 | Japan . |
| 1454105 | 10/1976 | United Kingdom . |
| 2122486 | 1/1984 | United Kingdom . |

OTHER PUBLICATIONS

H. Yoshida et al., "Absorption of Insulin Delivered to Rabbit Trachea Using Aerosol Dosage Form," *J. Pharm. Sciences*, vol. 68, No. 5, 670–671 (May 1979).

F.M. Wigley et al., "Insulin Across Respiratory Mucosae by Aerosol Delivery," *Diabetes*, vol. 20, No. 8, 522–556 (Aug. 1972).

N.C. Staub, "Preparation of Chronic Lung Lymph Fistulas in Sheep," *J. Surgical Res.*, 19, 315–320 (1975).

The Merck Manual of Diagnosis and Therapy, 11$^{th}$ Ed. pp. 763–765 (1966).

BioChem. and BioPhys. Res. Comm. vol. 139, No. 3, 1986, pp. 896–902, Roberts et al.

Journal of Immunology, vol. 119, No. 6, Dec. 1977, pp. 2137, Willoughby et al.

Journal of Immunology, vol. 121, No. 3, 1978, p. 926 Bvaley et al.

Journal of Immunology, vol. 124, No. 4, 1980, p. 1763, Shenker et al.

*Primary Examiner*—Christina Y. Chan
*Assistant Examiner*—T. D. Wessendorf
*Attorney, Agent, or Firm*—Leydig, Voit & Mayer, Ltd.

[57] ABSTRACT

Aerosolization of therapeutic proteins is demonstrated using recombinant $\alpha_1$-antitrypsin for treatment of emphysema as paradigmatic.

10 Claims, No Drawings

AEROSOLIZATION OF PROTEIN THERAPEUTIC AGENT

This is a continuation of application(s) Ser. No. 07/873,640 filed on Apr. 23, 1993, abandoned which is a continuation of Ser. No. 07/504,047 filed on Apr. 3, 1990, abandoned which is a continuation of Ser. No. 07/044,446 filed Apr. 30, 1987, abandoned.

INTRODUCTION

1. Technical Field

The subject field is the use of aerosolization for administration of proteinaceous drugs to the lungs.

2. Background

In the treatment of many diseases, there is a continuing problem of administration. Many therapeutic agents cannot be administered orally, since they will be subject to degradation or other processing in the digestive tract, resulting in loss of efficacy. Proteins are particularly sensitive to the action of proteases resulting in their hydrolysis and fragmentation. Another mode of administration which may be used is parenteral where the therapeutic agent may be injected at a variety of sites, such as subcutaneously, intraarterially, intravenously, intraperitoneally, or the like. For the most part, unless the diseased state is at the site of injection and in many cases even where the diseased state is at the site of injection, the drug is rapidly degraded and/or distributed throughout the vascular system. Thus, the host is systemically affected by the drug, where the major proportion of the drug merely serves to maintain a minimum level in the bloodstream, so that the diseased state is treated with a therapeutic dosage. Where drugs have side effects other than the desired result, and most drugs do, the result is substantial interference with normal bodily functions.

An alternative route which has been considered in some instances is administration intranasally which again results in systemic deposition of the drug, aerosolization. Where the concern is a diseased state of the lungs, the drug may be directly delivered to the diseased tissue by aerosolization and subsequent inhalation of the drug. However, even where one directs the drug to the lungs initially, there are substantial uncertainties about the efficacy in treating the lungs. The half-life of the drug in the lungs may be relatively short due to absorption into the vascular system. In addition, those drugs which are sensitive to enzymatic degradation or other processing, will be subject to modification and loss of efficacy. There is also the problem of the effect of aerosolization on the drug, where the drug may be degraded by the nebulizing action of the nebulizer or inactivated by oxidation. There is also the uncertainty of the distribution of the drug in the lungs, as well as the ability to maintain an effective dosage for an extended period, without detrimental effect to the lungs or other organs of the host.

RELEVANT LITERATURE

U.S. Pat. No. 4,599,311 describes the preparation of $\alpha_1$-antitrypsin by recombinant techniques.

A number of studies have been directed to aerosol inhalation to determine the effect and fate of antigenic proteins which were included in the aerosol. See for example, Brailey et al., *J. Immunol.* (1978) 121:926–929; Brailey et al., *J. Clin. Invest.* (1979) 63:1103–1109; and Dawson et al., *Chest* (1979) 75:(2 suppl.) 276–278 who studied the effects and fate of human serum albumin and ovalbumin. Willoughby and Willoughby, *J. Immunol.* (1977) 119:2137–2146; Willoughby et al., *Lab Invest.* (1979) 40:399–414; and Shenker et al., *J. Immunol.* (1980) 124:1763–1772 studied the effect and fates, either independently or combined, of the antigens Concanavalin A and bovine serum albumin. Other references concerned with antigens and aerosols include Karol. *Amm. Ind. Hyg. Assoc. J.* (1979) 40:283–290; Hogg et al., *Fed. Proc.* (1979) 38:197–201; and Higginbotham et al., *Food Chem. Toxicol.* (1983) 21:815–823.

The preparation of protein containing aerosols has been described by Przyborowsky, *Eur. J. Nucl. Med.* (1982) 7:71–72, as well as the above identified references.

The administration of insulin in an aerosol for th treatment of diabetes is described by Wigley et al., *Diabetes* (1971) 20:552–556 and Yoshida et al., *J. Pharm. Sci.* (1979) 670–671.

SUMMARY OF THE INVENTION

Proteinaceous therapeutic products are administered as an aerosol in the prophylactic or therapeutic treatment of diseased states of the lung. The invention is exemplified by the use of recombinant $\alpha_1$-antitrypsin to inhibit elastase, a proteolytic enzyme affecting lung tissue and implicated as a major cause of emphysema.

DESCRIPTION OF THE SPECIFIC EMBODIMENTS

Methods and compositions are provided for treating diseased states of the lung where the therapeutic agent is a protein, particularly a high molecular weight protein. Aerosol formulations are prepared of the protein to provide a physiologically effective dosage of the protein in the lungs to provide a prophylactic or therapeutic effective amount. It is found that the drugs are retained in the lung epithelial lining fluid, so as to maintain an effective concentration in the lung in contact with lung tissue for extended periods of time.

The subject invention is of particular interest in employing proteinaceous drugs which serve as serine protease inhibitors, particularly the use of $\alpha_1$-antitrypsin or active analog thereof as an inhibitor of elastase. The $\alpha_1$-antitrypsin may be used in the treatment of emphysema to prevent proteolytic attack on native lung tissue. The drugs which are employed may be naturally occurring, that is, isolated from natural sources, may be prepared by recombinant or synthetic techniques, may be mutants of naturally occuring drugs or non-naturally occurring drugs or combinations thereof.

The subject invention can be used with a variety of lung associated diseases where protein compositions may find application. The proteins for the most part will be not less than 5,000 molecular weight (5 kD), generally at least 15 kD molecular weight, usually at least about 20 kD molecular weight, more usually at least about 30 kD molecular weight, frequently exceeding 50 kD molecular weight, and may be 600 kD or more molecular weight, usually not exceeding about 500 kD molecular weight. Proteins which may find use include the various interferons, alpha, beta, and gamma, immunoglobulins, lipocortin, phospholipase inhibitors, atrialnaturetic factor, etc. These compounds may find application in such indications as pathogenic infection, including viruses, protists, prokaryotes, or the like. Diseases other than those directly related to infection which may be treated include asthma, adult or infant respiratory distress syndrome, emphysema, lung cancer, etc.

The aerosol formulation may be varied widely, depending upon the nature of the therapeutic agent, whether additional agents will be included, the manner and area in which it will be released in the lungs, or the like.

The amount of protein which is employed will usually vary from about 0.1 to 15, more usually 0.5 to 10, weight percent of the aerosol agent. Other components which may be included include excipients, which are water soluble and may also serve to enhance absorption. These additives include lactose. In addition, physiologically acceptable surfactants may be employed, particularly glycerides, more particularly diglycerides, where one of the carboxylic acids is of from 2 to 4 carbon atoms, and the other will be of from 12 to 20 carbon atoms, more usually of from 16 to 18 carbon atoms, either saturated or unsaturated.

The excipient may vary from about 0 to 80 weight percent of the formulation, while the surfactant may vary from about 10 to 50 weight percent of the formulation.

various physiologically acceptable inert gases may be employed as the aerosolizing agent or a nebulizer may be used to form the desired size aerosol particles. Where an inert gas is employed, such as polyhaloalkanes, e.g. dichlorodifluoromethane, dichlorotetrafluoroethane, etc., these will normally be present in about 0.5 to 5 weight percent.

For $\alpha_1$-antitrypsin, the amount employed will vary depending upon a number of factors, including the size of the particle, frequency of administration, nature of the disease, whether the treatment is for therapeutic or prophylactic purposes, etc. Usually the dosage will vary from about 1 µg to 10 mg/kg of host. The diameter of the particles will generally range from about 0.5 to 5 µm, preferably from about 1 to 3 µm. The period of treatment will vary widely, depending upon the therapeutic dosage, the concentration of the drug, the rate of administration, and the like. Generally, the period of administration will range from about 2 sec. to 30 min, more usually from 3 sec to 7 sec with metered dose inhalers and 10 to 20 min for nebulizers. A single administration or repeated administrations may be required. Thus, the aerosol may be administered one or more times at intervals from about 2 to 24 hours.

The following examples are offered by way of illustration and not by way of limitation.

EXPERIMENTAL

In order to demonstrate that recombinant $\alpha_1$-antitrypsin (rAAT) could be delivered to the lower respiratory tract and traverse the lung tissue, the following experiment was performed.
Surgical Procedure
An animal model was employed as described by Staub et al., *J. Surgical Res.* (1975) 19:315–320. By utilizing a chronic lung lymph fistula, nearly pure lung lymph may be isolated. Sheep are anesthetized with 0.5 g sodium pentothal, intubated, and ventilated with room air and 0.5–1% halothane. Catheters are installed in the carotid artery and jugular vein and a right thoracotomy is performed to install a chronic catheter in the afferent lymph duct from the caudal mediastinal node. The tail of the node is ligated and the systemic lymphatics along the diaphragm are cut to minimize the contribution of systemic lymph to the lymph that is collected. After closing the chest, the sheep are allowed to recover for 2–3 days before experimentation.

On the day of the test, the test sheep are anesthetized with sodium pentothal, intubated, and ventilated with room air and halothane as described previously. The appropriate amount of $\alpha_1$-antitrypsin as a 25 mg/ml rAAT in PBS is put into a Heyer Model USC77 ultrasonic nebulizer and the nebulizer is inserted in the inspired line from the ventilator to the sheep's endotracheal tube. With the sheep under the gamma camera and the ventilator set at a tidal volume of 19 ml/kg body weight the nebulizer is turned on to allow generation of the aerosol. After approximately 2 minutes, the nebulizer is turned off and removed from the circuit.

Once every 5 experiments, the size of the aerosol particle entering the endotracheal tube is measured by drawing a sample of the inspired air through a cascade impactor during the deposition period. The measurements show that the aerosol produced has a mass mean aerodynamic diameter of approximately 1.2 µm and a geometric standard deviation of 1.6.

Purified recombinant $\alpha_1$-antitrypsin (prepared essentially as described in U.S. Pat. No. 4,599,311) was administered intravenously or by aerosol to sheep (n=11) as previously described and the concentration of the $\alpha_1$-antitrypsin was measured in plasma, lung epithelial lining fluid (ELF) and lung lymph. Using a dose of 60 mg/kg, intravenous infusion resulted in lung ELF levels of 400±100 nM after 2 h. In contrast, using a nebulization system that generated greater than 95% of particles of less than about 5 µm and 34±2% less than 2 µm, a dose of only 2.5 mg/kg of aerosolized $\alpha_1$-antitrypsin resulted in the same ELF levels at 2 h (p>0.1). The aerosolized $\alpha_1$-antitrypsin appeared in lung lymph in a time dependent manner (1 h 2±1 nM, 2 h 13±6 nM, 3 h 27±17 nM, 4 h 117±30 nM), driven by a concentration gradient in ELF (2 h 400±50 nM).

The above results demonstrate that the $\alpha_1$-antitrypsin can be aerosolized into sufficient sized particles to provide therapeutic dosage levels of proteins, to access the alveolar spaces and in vivo reach the epithelial surface and interstitium of the lower respiratory tract. Thus, the aerosolized administered $\alpha_1$-antitrypsin can augment the anti-elastase defenses related to protection against inflammatory action and prevent attack of normal tissue.

The success demonstrated above is paradigmatic of the fact that a high molecular weight protein that is oxidation sensitive can be aerosolized and retain its activity. The protein may be delivered to the lower respiratory tract in active form. Aerosolization provides for transport of large proteins through the lung epithelial lining to the lung interstitium and final delivery to the blood for clearance. The aerosolization is able to provide for protection of the molecule from degradation by tissue proteases or cellular uptake. The aerosol administered protein also appears to be protected from rapid removal and/or inactivation for extended periods of time to allow for long-term effectiveness, so as to reduce the required number of administrations.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for augmenting the inhibition of elastase in an individual comprising administering to the lungs of an individual a therapeutically effective amount of aerosolized particles, wherein said particles consist essentially of naturally occurring isolated and purified $\alpha_1$-antitrypsin or recombinant $\alpha_1$-antitrypsin which are in the range of about 0.5 to about 5 micrometers in diameter, such that said $\alpha_1$-antitrypsin is retained in the lung epithelial lining fluid or lung lymph.

2. The method according to claim 1, wherein said particles are in the range of about 1 to about 3 micrometers in diameter.

3. The method according to claim 1, wherein said $\alpha_1$-antitrypsin is recombinant $\alpha_1$-antitrypsin.

4. A method for augmenting the inhibition of elastase in an individual comprising administering to the lungs of an individual a therapeutically effective amount of aerosolized particles consisting essentially of naturally occurring isolated and purified $\alpha_1$-antitrypsin or recombinant $\alpha_1$-antitrypsin of about 0.1 to about 15 weight percent of an aerosol agent, such that said $\alpha_1$-antitrypsin is related in the lung epithelial lining fluid or lung lymph.

5. The method according to claim 4, wherein said $\alpha_1$-antitrypsin is about 0.5 to about 10 weight percent of said aerosol agent.

6. A method of treating emphysema in an individual comprising administering to the lungs of an individual a therapeutically effective amount of aerosolized particles, wherein said particles consist essentially of naturally occurring isolated and purified $\alpha_1$-antitrypsin or recombinant $\alpha_1$-antitrypsin which are in the range of about 0.5 to about 5 micrometers in diameter, such that said $\alpha_1$-antitrypsin is retained in the lung epithelial lining fluid or lung lymph.

7. The method according to claim 6, wherein said particles are in the range of about 1 to about 3 micrometers in diameter.

8. The method according to claim 6, wherein said $\alpha_1$-antitrypsin is recombinant $\alpha_1$-antitrypsin.

9. A method of treating emphysema in an individual comprising administering to the lungs of an individual a therapeutically effective amount of aerosolized particles consisting essentially of naturally occurring isolated and purified $\alpha_1$-antitrypsin or recombinant $\alpha_1$-antitrypsin of about 0.1 to about 15 weight percent of an aerosol agent, such that said $\alpha_1$-antitrypsin is retained in the lung epithelial lining fluid or lung lymph.

10. The method according to claim 9, wherein said $\alpha_1$-antitrypsin is about 0.5 to about 10 weight percent of said aerosol agent.

* * * * *